United States Patent [19] | [11] Patent Number: 4,871,693
Inoue et al. | [45] Date of Patent: * Oct. 3, 1989

[54] POROUS CORDIERITE CERAMICS

[75] Inventors: Senya Inoue, Saitama; Akira Ono, Tokyo; Mikio Kobayashi, Saitama; Hiroshi Yokoo, Tokyo, all of Japan

[73] Assignee: Kanto Kagaku Kabushiki Kaisha, Tokyo, Japan

[*] Notice: The portion of the term of this patent subsequent to Oct. 6, 2004 has been disclaimed.

[21] Appl. No.: 100,998

[22] Filed: Sep. 24, 1987

Related U.S. Application Data

[62] Division of Ser. No. 726,325, Apr. 23, 1985, Pat. No. 4,698,317.

[30] Foreign Application Priority Data

Apr. 24, 1984 [JP] Japan .................................. 59-81180
Apr. 24, 1984 [JP] Japan .................................. 59-81181
Dec. 21, 1984 [JP] Japan .................................. 59-268442

[51] Int. Cl.$^4$ ............................................ C04B 38/08
[52] U.S. Cl. .......................................... 501/9; 501/12; 501/39; 501/118; 501/119; 501/80; 502/527
[58] Field of Search ............................. 501/33, 80–85, 501/39, 9, 12, 118, 119; 502/527; 423/329

[56] References Cited

U.S. PATENT DOCUMENTS

| 2,797,201 | 6/1957 | Veatch et al. | 106/86 |
| 3,030,215 | 4/1962 | Veatch et al. | 501/33 |
| 3,347,798 | 10/1967 | Baer et al. | 502/527 |
| 3,950,175 | 4/1976 | Lachman et al. | 501/80 |
| 4,021,253 | 5/1977 | Budrick | 501/12 |
| 4,257,799 | 3/1981 | Rosenchwaig et al. | 65/21.4 |
| 4,367,292 | 1/1983 | Sano et al. | 501/119 |
| 4,374,044 | 2/1983 | Schaeffer et al. | 502/80 |
| 4,547,468 | 10/1985 | Jones et al. | 501/33 |
| 4,560,660 | 12/1985 | Geirnaert | 501/118 |
| 4,698,317 | 10/1987 | Inoue et al. | 501/119 |

Primary Examiner—William R. Dixon, Jr.
Assistant Examiner—Karl Group
Attorney, Agent, or Firm—Birch, Stewart, Kolasch & Birch

[57] ABSTRACT

New type porous cordierite ceramics having a new characteristic interconnecting open cellular structure and a hollow microspherical cordierite glass powder with a shell devoid of any pores or provided with a few or an abundance of open pores which is used as a starting material for the porous cordierite ceramics. The porous cordierite ceramics are produced by subjecting a starting solution containing an alkyl silicate, an aluminum salt and an magnesium salt optionally with other compounds in an organic or aqueous organic solvent to spray thermal decomposition to prepare the hollow microspherical cordierite glass powder, and then processing the cordierite glass powder to a shaped body after or before an optional heat treatment and firing the shaped body at a temperature below the melting point of cordierite. The porous cordierite ceramics are useful as a carrier for gas chromatography or various chemical reactions.

8 Claims, 6 Drawing Sheets

$(2\theta)$

$(2\theta)$

POROUS CORDIERITE CERAMICS

This application is a divisional of copending application Ser. No. 726,325, filed on Apr. 23, 1985, now U.S. Pat. No. 4,698,317.

BACKGROUND OF THE INVENTION

1. Field of the Invention:

The present invention relates to new type porous cordierite ceramics having a new characteristic interconnecting open cellular structure. The present invention relates also to a hollow microspherical cordierite glass powder devoid of any pore or provided with an abundance of open pores in a shell thereof, which is suitable as a starting material for producing the porous cordierite ceramics and to a process for producing same by spray thermal decomposition of a starting solution. The present invention relates further to a use of a porous cordierite ceramics as a carrier for gas chromatography or various chemical reactions, e.g. catalytic or biochemical reactions.

2. Description of the Prior and Related Arts:

From the past, porous cordierite ceramics distinguished by their excellent thermal shock resistance and chemicalsresisting property have widely been utilized, usually after being processed to various shaped bodies, as heat insulating materials, filters, catalyst supports and carriers on which enzymes or microbes are immobilized. In this case, porosity of the cordierite ceramics largely contributes to their useful applications. In order to enhance the function of these useful materials, a precise control is required for various factors with respect to porosity of such cordierite ceramics. In fact, many attempts have been made to control the size of pores, pore volume, pore size distribution, shape of pores and pore structure of cordierite ceramics. Up to the present, however, none of the prior arts reported hitherto succeeded in controlling all of these factors.

On the other hand, inorganic hollow glass spheres are utilized as light-weight aggregates, carriers for catalysts and heat-insulating materials. Such inorganic hollow glass spheres are generally manufactured by softening a powdery gel as a film-forming material or a naturally occurring glass-forming material such as a volcanic ash under heating and foaming the softened material. In addition to such foaming method under heating, various methods have been proposed for producing hollow spherical substances. Among the methods using a starting material in the form of a solution or slurry, some utilize a volatile liquid vehicle and others utilize chemical reactions resulting from pyrolysis. Concerning the latter-mentioned mode of reaction, a number of methods for producing powdery substances have long been used wherein a solution or slurry of starting materials is subjected to spray thermal decomposition. This "spray thermal decomposition" itself is already known for some 50 years ago and widely used for producing metal oxides from salts, especially in the field of metallurgy. Depending on the conditions, products of spray thermal decomposition are obtained in the form of hollow microspheres. Thus, several prior art techniques are known as a means for producing hollow vitreous microspheres according to spray thermal decomposition. In U.S. Pat. No. 2,797,201, for example, there is disclosed a method for producing hollow spherical shells by preparing a solution of a film-forming substance and a foaming substance in a volatile solvent and atomizing the solution into a spray drying column from a top thereof whereby droplets of the solution were heated countercurrently by a hot blast while descending, to permit evaporation of the solvent and poreless spherical shells are collected at the bottom of the column. According to the method disclosed in U.S. Pat. No. 2,978,339 wherein a solvent is not used as a mixture medium, fine solid particles obtained by mixing a substance capable of producing glass by fusion with a foaming agent is introduced upwardly into a vertical furnace wherein the particles are fused by a high temperature gas to form hollow vitreous microspheres. U.S. Pat. No. 3,030,215 discloses a method of producing hollow spherical glass powders wherein a slurry containing water glass, zinc oxide, boron oxide, a foaming agent, etc. is dried at about 300° C. for 16 hours and ground, and the resultant particles are foamed in an up-draft maintained at about 1100° C. whereby hollow spherical glass powders are blown up and collected at the top of the up-draft. Further, U.S. Pat. No. 4,021,253 discloses a method of producing a similar hollow spherical glass powder wherein a gel containing a silica sol (Ludox), sodium methoxide, boric acid and urea or a gel obtaining by hydrolyzing ethyl silicate, lead acetate, sodium acetate, potassium acetate, calcium chloride and urea is dried, ground and sieved and the resultant particles of a definite size are then foamed under heating. Recently, U.S. Pat. No. 4,257,799 discloses a method of producing hollow spherical glass powders wherein a solution of a silicate glass-forming substance is dropped within a vertical furnace the temperature of which is precisely controlled, whereby droplets of the solution are solidified and foamed under heating to form hollow spherical glass powders. All of the methods disclosed in these references contemplate the production of hollow spherical glass particles by foaming the raw material under heating optionally by the aid of a foaming agent but do not relate to cordierite glass powders. Furthermore, these prior and related arts contemplate the production of hollow spheres with a shell devoid of any pore therein.

From the past, a general method for producing porous cordierite ceramics comprises crushing and grinding cordierite or starting materials such as silica-alumina-magnesia, magnesite-kaolin or talc-alumina-kaolin, subjecting the ground particles to a sieving treatment to collect particles of a definite size, mixing them with a binder, and then molding and sintering the mixture. In this case, porosity of the sintered bodies results from a number of interstices remaining between the sintered particles. Another general method for producing porous cordierite ceramics comprises mixing cordierite or such starting materials with a combustible substance or a foaming agent and then molding and sintering the mixture. In this case, the pore structure results from interstices and pores formed by combustion or pyrolysis of the combustible substance or foaming agent. Inasmuch as physical properties such as mechanical strength, thermal shock resistance, etc. of the porous cordierite ceramics are largely influenced by porosity, pore size, pore volume, pore distribution, shape of pores, etc., controlling of these pore factors is recently demanded for the porous cordierite ceramics especially for use in catalytic reactions. In U.S. Pat. No. 3,950,175 there is disclosed a method of controlling pore size of porous cordierite ceramics wherein kyanite, pyrophilite, quartz and/or fused silica is substituted for talc or clay in the raw material and the substituted raw material is fired at 1340°–1450° C. to yield a cordierite ceramic having at least 20% open pores larger than 10 μ in diameter. Recently, U.S. Pat. No. 4,374,044 discloses a method for producing a high strength, high macro-pore volume porous cordierite ceramics wherein a usual dry clay raw material containing talc, clay and alumina preferably with an organic binder is subjected together with a colloidal silica diluted with water to disc pelletizing to form green pellets which are then dried to remove free water and fired at 1390°–1410° C. whereby any organic binder contained is burnt out.

According to the conventional methods for producing porous cordierite ceramics, a dry clay mixture which may partially be substituted by a similar ingredients is commonly used as a raw material and is fired at about 1400° C. without using the so-called "spray thermal decomposition" method, even in the methods recently reported in the above-mentioned U.S. patents. Particularly noteworthy here is that in the production of porous cordierite ceramics, the pore size and/or pore volume may be controlled by the recently developed methods but control of the shape of pores and the pore structure in addition to the above pore characteristics has never been achieved hitherto. As the function of the porous cordierite ceramics as carriers for various purposes is largely influenced by all of the pore characteristics, there is a great demand for developing a method for controlling all of the pore characteristics of hollow microspherical cordierite glass powders and porous cordierite ceramics.

BRIEF SUMMARY OF THE INVENTION

Accordingly, it is an object of the present invention to provide new type porous cordierite ceramics having a new characteristic interconnecting open cellular structure.

It is another object of the present invention to provide a hollow microspherical cordierite glass powder devoid of any pore or provided with an abundance of pores on a shell thereof which is suitable as a starting material for producing the porous cordierite ceramics.

It is still another object of the present invention to provide a process for the production of the hollow microspherical cordierite glass powder wherein an aqueous organic solution of starting materials of cordierite is subjected to spray thermal decomposition.

It is further object of the present invention to provide a method for controlling various factors for pore characteristics of the hollow microspherical cordierite glass powder by adjusting the preparation conditions therefore to yield the product having shells with or without pores.

It is yet a further object of the present invention to provide a use of the porous cordierite ceramics as a carrier for gas chromatography.

It is still a further object of the present invention to provide a use of the porous cordierite ceramics as a carrier on which a catalyst is supported or enzymes or microbes are immobilized.

These and other objects, features and advantages of the present invention will become apparent more fully from the following description.

As a result of extensive research made by the present inventors for developing a method for controlling various factors for pore characteristics of a hollow microspherical cordierite glass powder as a raw material for the porous cordierite ceramics, it has now been found that a hollow microspherical cordierite glass powder with various pore characteristics can be obtained when an organic or aqueous organic solution containing an alkyl silicate, an aluminum salt and a magnesium salt in a proportion capable of affording a theoretical composition of cordierite is subjected together with an oxidizing gas to spray thermal decomposition. The cordierite glass powder thus produced is in the form of hollow spherical shells devoid of any pore or provided with a few or an abundance of open pores which exist in the latter case in a honeycomb-like structure. This hollow spherical cordierite glass powder is then processed to a shaped body by molding or other shaping means, after an optional heat treatment conducted at a temperature below 950° C., and fired at a temperature between 950° C. and 1450° C. to form the porous cordierite ceramics.

In one embodiment of the present invention, there is provided new type porous cordierite ceramics fundamentally with a chemical composition of cordierite having a new characteristic interconnecting open cellular structure and a process for producing the porous cordierite ceramics which comprises subjecting a starting solution to spray thermal decomposition in the presence of an oxidizing gas to form a hollow microspherical cordierite glass powder, processing the glass powder to a shaped body after an optional heat treatment, and thereafter firing the shaped body, the starting solution containing in an organic or aqueous organic solvent an alkyl silicate and aluminum and magnesium salts soluble in the organic solvent in a proportion of 44–65% by weight, 25–43% by weight and 10–16% by weight in terms of $SiO_2$, $Al_2O_3$ and $MgO$, respectively.

In another embodiment of the present invention, there is provided a hollow microspherical cordierite glass powder devoid of any pore or provided with a few or an abundance of open pores in a shell thereof and a process for producing the hollow spherical cordierite glass powder which comprises subjecting a starting solution to spray thermal decomposition in the presence of an oxidizing gas, the starting solution containing in an organic or aqueous organic solvent an alkyl silicate and aluminum and magnesium salts soluble in the organic solvent in a proportion of 44–65% by weight, 25–43% by weight and 10–16% by weight in terms of $SiO_2$, $Al_2O_3$ and $MgO$, respectively, and optionally subjecting the resultant cordierite glass powder to a heat treatment.

In still another embodiment of the present invention, there is provided a use of the porous cordierite ceramics, which may contain in addition to a chemical composition of cordierite $Na_2O$, $K_2O$, $TiO_2$ and/or $ZrO_2$ in an amount up to 5% by weight based on cordierite, as a carrier for gas chromatography or for catalytic or biochemical reactions.

BRIEF DESCRIPTION OF THE DRAWINGS

FIGS. 1(a)–1(d) are graphs showing X-ray diffraction patterns of powder samples obtained by pulverizing cordierite produced according to a conventional method by melting individual constituents, with FIG. 1(a) being a graph showing an X-ray diffraction pattern of the sample, FIG. 1(b) being a similar graph of the sample subjected to a heat treatment at 900° C., FIG. 1(c) being a similar graph of the sample subjected to a heat treatment at 950° C.

FIGS. 3(a)-3(d) are graphs showing X-ray diffraction patterns of powder samples obtained according to the process of this inventing by subjection a starting solution to spray thermal decomposition, with FIG. 3(a) being a graph showing an X-ray diffraction pattern of the sample, FIG. 3(b) being a similar graph of the sample subjected to a heat treatment at 900° C., FIG. 3(c) being a similar graph of the sample subjected to a heat treatment at 950° C.

DETAILED DESCRIPTION OF THE INVENTION

The porous cordierite ceramics basically have a theoretical composition of cordierite which is shown by an empirical formula: $2MgO \cdot 2Al_2O_3 \cdot 5SiO_2$. According to F. Singer [Singer, F. : British Clayworker, 66 19 (1957)], the proportion of the constituents is 51.4-64.9% by weight for $SiO_2$, 25.5-38.8% by weight for $Al_2O_3$ and 2.6-13.8% by weight for MgO. With a view to modifying the characteristics of the porous cordierite ceramics, however, it is possible to select a different chemical composition by somewhat changing the proportion of the constituents in such manner that the hollow spherical cordierite glass powder obtained by spray thermal decomposition shows a halo pattern only by an X-ray diffraction analysis and a glass-like property by a differential thermal analysis (DTA) but will contain cordierite as a major crystalline phase with slight over crystalline phases when heated to a higher temperature to cause crystallization. In the present invention, it is a matter of course that porous cordierite ceramics having such modified compositions are also involved in the scope of the porous cordierite ceramics of the present invention.

On the other hand, the hollow microspherical cordierite glass powder, i.e. the cordierite glass powder in the form of balloon-like spheres of the present invention is produced from the constituents having a composition of 44-65% by weight for $SiO_2$, 25-43% by weight for $Al_2O_3$ and 10-16% by weight for MgO by spray thermal decomposition. The glass powder shows characteristics of glass in either of X-ray diffraction analysis and DTA and will crystallize exclusively as cordierite crystals or mainly as cordierite crystals with a smaller proportion of other crystals when heated at a higher temperature. All types of hollow microspherical cordierite glass powder are involved in the scope of the cordierite glass powder of the present invention so far as they form porous ceramics containing cordierite crystalline phase alone or in a predominant proportion when the glass powder is heated at a temperature higher than the crystallization temperature.

In the present invention, other ingredients usually incorporated into the cordierite constituents to modify the characteristics of the cordierite glass powder or ceramics are one or more compounds capable of affording $Na_2O$, $K_2O$, $TiO_2$ and/or $ZrO_2$ and are used as a rule in an amount up to 5% by weight based on cordierite.

As the porous cordierite ceramics of the present invention are produced from the hollow microspherical cordierite glass powder by firing, it follows that the process for producing the ceramics starts with the preparation of the cordierite glass powder. Thus, the present invention is explained in detail hereinafter in this preparative order.

In the present invention, the preparation of the hollow microspherical cordierite glass powder is characterized by subjecting a starting solution to spray thermal decomposition conducted for a very short period of time at a remarkably low temperature in a simple operation as compared with a conventional method wherein a cordierite glass powder is produced by melting individual constituents and pulverizing the resultant solid mass. As the starting material for the glass powder is in the form of a solution, all of the ingredients can homogeneously be mixed so that a small amount of any necessary additive for improving or modifying the thermal, chemical and/or mechanical characteristics of the cordierite glass powder, such as a compound capable of affording $Na_2O$ or $TiO_2$, can be added to the solution and homogeneously mixed therein with the fundamental constituents for cordierite in a simple manner.

A liquid medium used for the starting solution is a volatile organic solvent freely or easily miscible with water. Such organic solvent is selected from a lower alkanol with 1-5 carbon atoms, a dihydric or trihydric lower alcohol, a (lower alkoxy) lower alkanol and a lower dialkyl ketone. The alkyl moiety of these compounds may have straight or branched chain. Illustrative of the organic solvent are, for example, methanol, ethanol, n-propanol, isopropanol, n-butanol, isobutanol, tert-butanol, n-pentanol and isopentanol as the straight or branched chain lower alkanol; ethylene glycol, propylene glycol and glycerol as the dihydric or trihydric lower alkanol; 2-methoxyethanol, 2-ethoxyethanol and 3-methoxy-n-propanol as the (lower alkoxy) lower alkanol; and acetone, methyl ethyl ketone and hexone as the lower dialkyl ketone. The use of a lower alkanol, especially methanol, ethanol or isopropanol is particularly preferable. These organic solvents may be used singly or as a mixture of at least two, e.g. a mixture of ethanol and 2-methoxyethanol (1:1). The organic solvents may contain water in an amount up to 50% by weight, preferably 20% by weight. The use of water is rather necessary in certain cases as will be described hereinafter and so the content of water must precisely be adjusted in such cases not only for the organic solvents but also for metal compounds used. In general, these organic solvents are commercially available as anhydrous ones but some commercially available organic solvents such as ethanol often contain a trace or small amount of water according to grades or purposes. In the latter case, a definite amount of water can further be added to the organic solvent to prepare an aqueous organic solvent in which the content of water is adjusted to a desired value.

The fundamental constituents for producing cordierite used in the process of this invention are an alkyl silicate, an aluminum salt soluble in the organic solvent and a magnesium salt soluble in the organic solvent. Among these constituents, the alkyl silicate is used in an amount within the range of 44-65% by weight in terms of $SiO_2$, the aluminum salt in an amount within the range of 25-43% by weight in terms of $Al_2O_3$ and the magnesium salt in an amount within the range of 10-16% by weight in terms of $MgO$. It is one of the features of the present invention to use an alkyl silicate as a compound capable of affording the $SiO_2$ component for cordierite. The alkyl moiety of the alkyl silicate is selected from lower alkyls with 1-5 carbon atoms. Examples of the alkyl silicate include tetramethyl silicate, tetraethyl silicate, tetra-n-propyl silicate, tetraisopropyl silicate, tetra-n-butyl silicate and tetrapentyl silicate. The use of tetraethyl silicate or tetramethyl silicate is preferable. These silicates may be used singly or as a mixture of at least two. The aluminum salts and the magnesium salts are required to be soluble in the organic solvent used, and from this viewpoint, salts are as a rule nitrates and halides. Illustrative of the utilizable aluminum and magnesium salts are, for example, aluminum nitrate, aluminum chloride, aluminum bromide, magnesium nitrate, magnesium chloride and magnesium bromide. The use of the nitrates or chlorides is preferable. These three constituents for cordierite are dissolved in the above mentioned proportion in the organic or aqueous organic solvent to prepare a starting solution.

On the preparation of the starting solution by dissolving the constituents for cordierite in the organic solvent, the use of anhydrous aluminum and magnesium salts will keep the starting solution substantially free of water. On the other hand, the use of the aluminum and magnesium salts with water of crystallization will apparently increase the content of water in the starting solution even if a substantially anhydrous organic solvent alone is used. Depending on the sorts of the organic solvents and the metal salts used, solubility of the metal salts in the organic solvent becomes poor. Thus, a small amount of water contained in the organic solvent, which results from water of crystallization or is added purposely to form an aqueous organic solvent, serves to promote dissolution of the metal salts. In case solubility of the metal salts in the organic solvent is poor, the use of such aqueous organic solvent is particularly desirable to form a homogeneous starting solution. However, the content of water in the starting solution has a strong influence on the porosity of a hollow microspherical cordierite glass powder to be obtained and so the content of water has to be limited or adjusted according to the porosity desired in the glass powder.

The starting solution may be incorporated with a small amount of one or more metal compounds other than those used as the constituents for cordierite, with a view to improving sinterability of the glass powder or modifying the characteristics of the cordierite ceramics as a carrier for various purposes. Such metal compounds can afford $Na_2O$, $K_2O$, $TiO_2$ or $ZrO_2$ and are used in an amount up to 5% by weight in terms of the metal oxide based on the cordierite. These metal compounds are also required to be soluble in the organic or aqueous organic solvent to prepare a homogeneous starting solution. Illustrative of the metal compound are sodium nitrate, potassium nitrate and tetraisopropyl orthotitanate. Sodium nitrate or potassium nitrate is usually used in an amount up to 1% by weight and the titanium compound is used for imparting better physicochemical characteristics to a carrier for immobilization of enzymes or microbes.

In the starting solution the proportion of the compounds as the constituents for cordierite and of the other optional metal compounds can freely be varied within the defined ranges according to the intended purpose. The starting solution can be used in the process of this invention so far as it forms a clear homogeneous solution. In the starting solution, the concentration of the constituents for cordierite is within the range of 0.1-3.0 mols/l., preferably 0.5-2.0 mols/l, to facilitate the spraying operation.

The spray thermal decomposition of the starting solution is carried out by spraying the solution through a spray nozzle into a heated reaction zone previously maintained at a temperature above 700° C. by an electric or gas furnace or into the flame of a gas burner. This operation itself is carried out in a conventional manner in the presence of an oxidizing gas. Preferable examples of the oxidizing gas are oxygen and air. The use of compressed air is preferable since it has a dual function as an oxidizing gas and as a propellant for atomizing the starting solution. In a preferable embodiment, the starting solution is atomized together with a flow of compressed air into a heated reaction zone positioned vertically or horizontally and preheated with an electric furnace or into the flame of a gas burner through a cocentric two-fluid nozzle at given flow rates, whereby the atomized droplets of the solution with a diameter less than 100 microns are instantaneously heated to permit evaporation followed by combustion of the solvent and the residual mists of the solid substances are instantaneously pyrolyzed to form a hollow microspherical cordierite glass powder. The powdery product thus formed is entrained in a flow of compressed air and collected in a cyclon from the gaseous stream.

Figure 5:
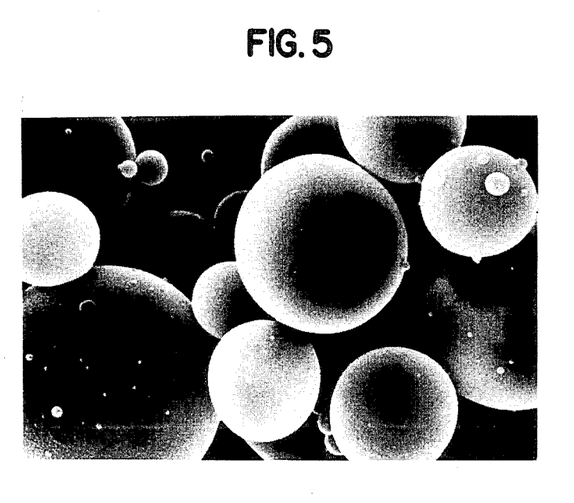
FIG. 5 is a scanning electron micrograph showing the state of balloon-like spheres of an example of the cordierite glass powder obtained according to the process of this invention. In this example, each balloon shell is devoid of any open pores.
Figure 7:
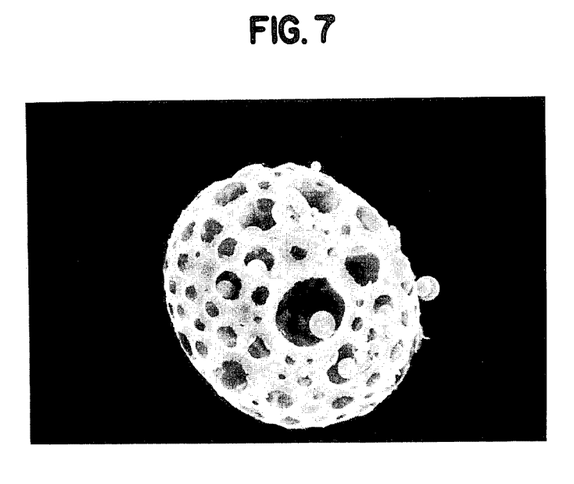
FIG. 7 is a scanning electron micrograph showing the state of balloon-like sphere of another example of the cordierite glass powder obtained according to the process of this invention. In this example, the balloon shell are provided with a plenty of open pores having a honeycomb-like structure.

It has now been found by the present inventors that the cordierite glass powder produced from the starting solution by spray thermal decomposition has a new hollow microspherical (balloon-like) structure and that a few or plenty of open pores can be formed in the balloon-like shell by adjusting the content of water in the starting solution. The hollow microspheres (balloon-like spheres) formed by the spray thermal decomposition are almost same in size as the droplets of the starting solution on spraying. In some cases, the resultant hollow microspheres are somewhat shrinked from the original size of the droplets of the starting solution. The droplets of the starting solution undergo instantaneous heating to cause evaporation of the solvent to form hollow microspheres of the solid substances in the solution. The hollow microspheres are then subjected to thermal decomposition whereby the solid substances are decomposed and converted to cordierite to form hollow microspheres with shells having a smooth surface as shown in FIG. 5. When water is present in a large or relatively large amount in the starting solution, hollow microspheres of the solid substances cannot form shells with a smooth uniform surface in the course of their thermal decomposition and conversion to cordierite glass because of rapid evaporation of water, and as the result, a few or plenty of open pores are formed in the shells by the water present within the hollow microspheres which bursts out of the shells, forming outwardly opened holes penetrating the shells. In case a plenty of open pores are formed in the shells, the shape of the open pores has a honeycomb-like structure as shown in FIG. 7. The size of the balloon-like spheres, the thickness of the shells and the number and size of open pores formed in the shells can suitably be adjusted according to the intended use of controlling the various conditions for spray thermal decomposition, e.g. the composition and concentration of the starting solution, the content of water in the starting solution, and spraying and pyrolyzing conditions. This point is another feature of the present invention. The reason why the cordierite glass powder is obtained in the process of this invention in the form of hollow microspheres is ascribable to the fact that very small droplets of the starting solution formed by spraying undergo instantaneous heating to cause evaporation of the solvent and are spherilized to form hollow microspheres unlike the conventional foaming method wherein the powdery starting material is foamed under heating by evaporation of water of crystallization in the starting material.

It has also been found by the present inventors that the content of water in the starting solution generally has a strong influence on the porosity of the resulting hollow spherical cordierite glass power as described above but this tendency varies according to a combination of the organic solvent and the constituents for cordierite. In a system of tetraethyl silicate-aluminum nitrate-magnesium nitrate-isopropanol, for example, the product (the cordierite glass powder) in the form of a balloon with a shell of a smooth surface devoid of any pores is obtained when the content of water in the starting solution is below 4% by weight, but the product in the form of a balloon with a shell having a plenty of open pores formed in a honeycomb-like structure is obtained when the content of water is above 4% by weight. Similarly, in a system of tetramethyl silicate-aluminum nitrate-magnesium nitrat-methanol, the product in the form of a balloon with a poreless shell is obtained when the content of water in the starting solution is below 8% by weight, but the product in the form of a balloon with a shell having open pores in a honeycomb structure is obtained when the content of water is above 8% by weight. In a system of tetraethyl silicate-aluminum chloride-magnesium chloride-ethanol, the product in the form of a balloon with a poreless shell is obtained when the content of water in the starting solution is about 15% by weight, but the product in the form of a balloon with a shell having open pores in a honeycomb structure is obtained when the content of water is more than about 15% by weight. Further, in a system of tetraethyl silicate-aluminum nitrate-magnesium nitrate an aqueous organic solvent in which the organic solvent is 2-methoxyethanol, ethylene glycol or glycerol:ethanol (1:1) or acetone, the product in the form of a balloon with a poreless shell is obtained even if the content of water in the solution is increased up to 25% by weight. The content of water for obtaining balloons with poreless shells thus varies according to a combination of the solvent and the constituents for cordierite. In any of the combinations, however, there is found such a tendency that balloons with poreless shells are formed until the content of water reaches to a certain level, but balloons with shells having open pores are formed when the content of water exceeds that level. Thus, the cordierite glass powder in any of the forms can be obtained by adjusting the content of water in the starting solution according to a combination of the solvent and the ingredients to be dissolved therein. Thus, it is possible to adjust the composition of the starting solution properly according to the intended purpose of porous cordierite ceramics to be produced.

The technical idea of forming a few or an abundance of open pores in the shells of the cordierite balloons has not yet been reported in any of the references published. This attempt has been attained for the first time by the present invention by using the starting materials in the form of a solution and conducting spray thermal decomposition of the solution under specific conditions. The process of the present invention for preparing the cordierite glass powder in such form is also different from the existing methods wherein the constituents are fired in a powdery form.

Figure 1A:
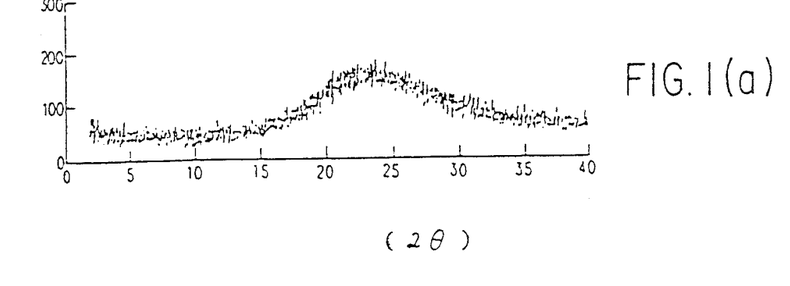
Figure 1B:
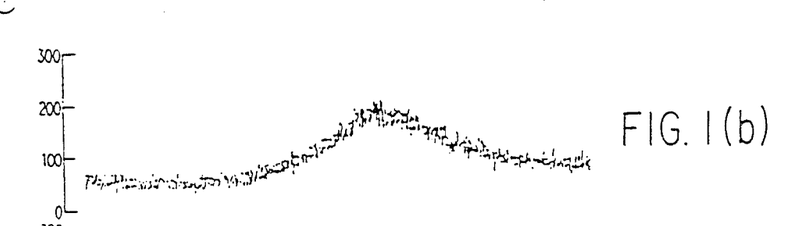
Figure 1C:
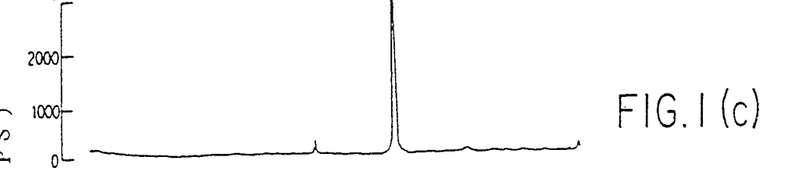
Figure 1D:
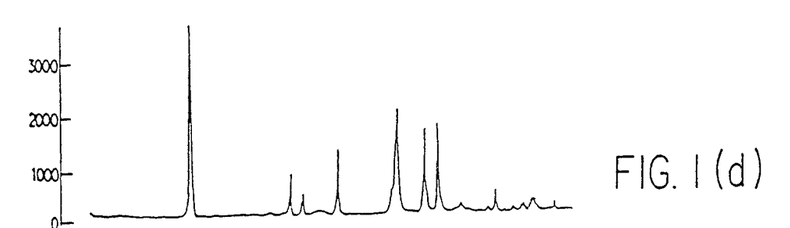
FIG. 1(d) being a similar graph of the sample subjected to a heat treatment at 1050° C. In each graph the abscissa stands for diffraction angle ($2\theta$) and the ordinate for diffraction intensity (CPS).
Figure 2:
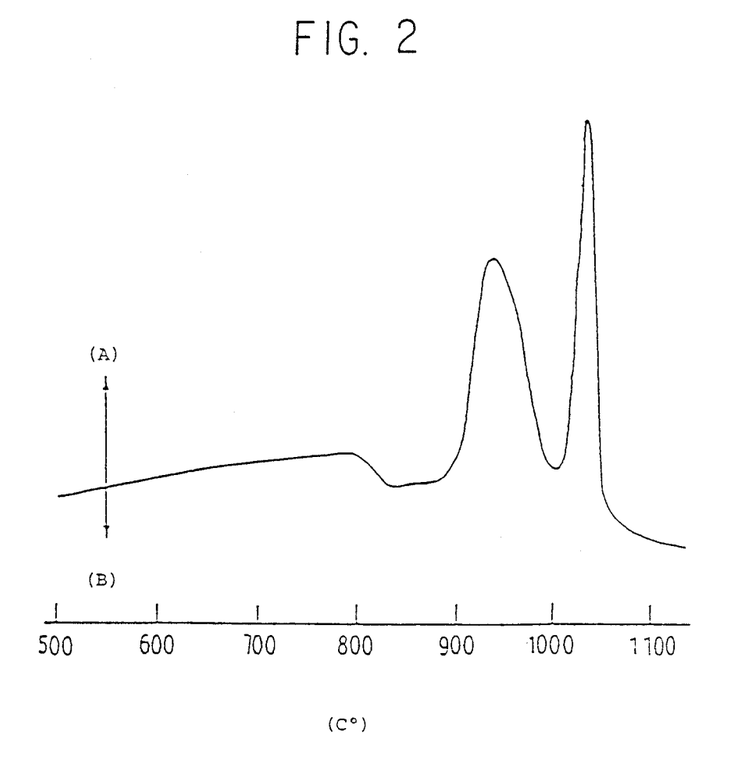
FIG. 2 is a graph showing a DTA chart of the same sample as used in the X-ray diffraction test shown in FIG. 1(a). In the graph the abscissa stands for temperature (°C) and a region (A) above the curve is exothermic and a region (B) below the curve is endothermic.
Figure 3A:
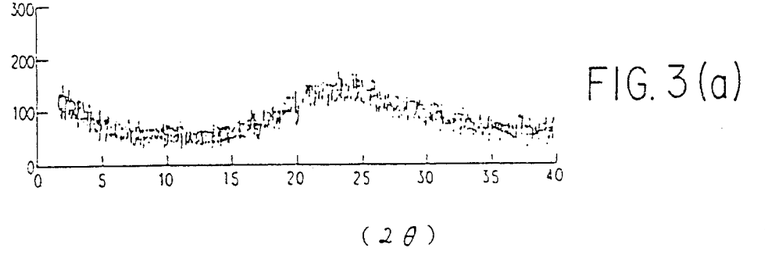
Figure 3B:
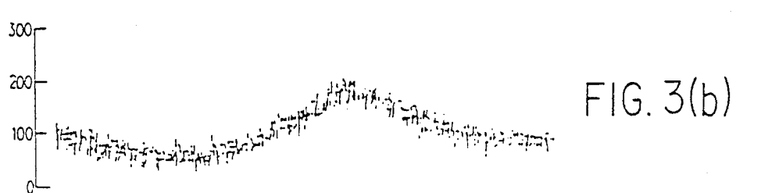
Figure 3C:
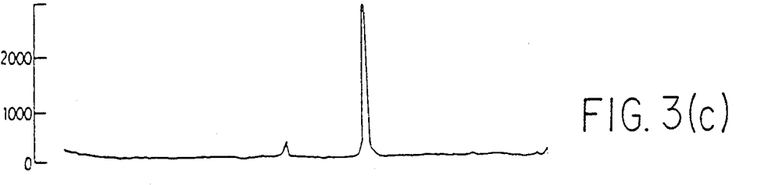
Figure 3D:
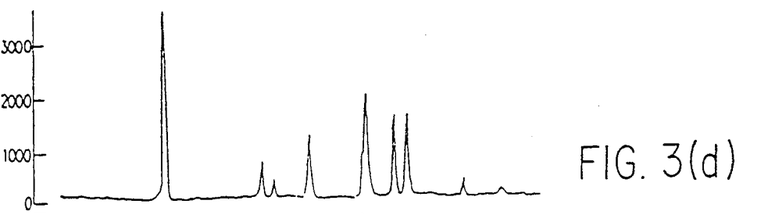
FIG. 3(d) being a similar graph of the sample subjected to a heat treatment at 1050° C. In each graph the abscissa stands for diffraction angle ($2\theta$) and the ordinate for diffraction intensity (CPS).
Figure 4:
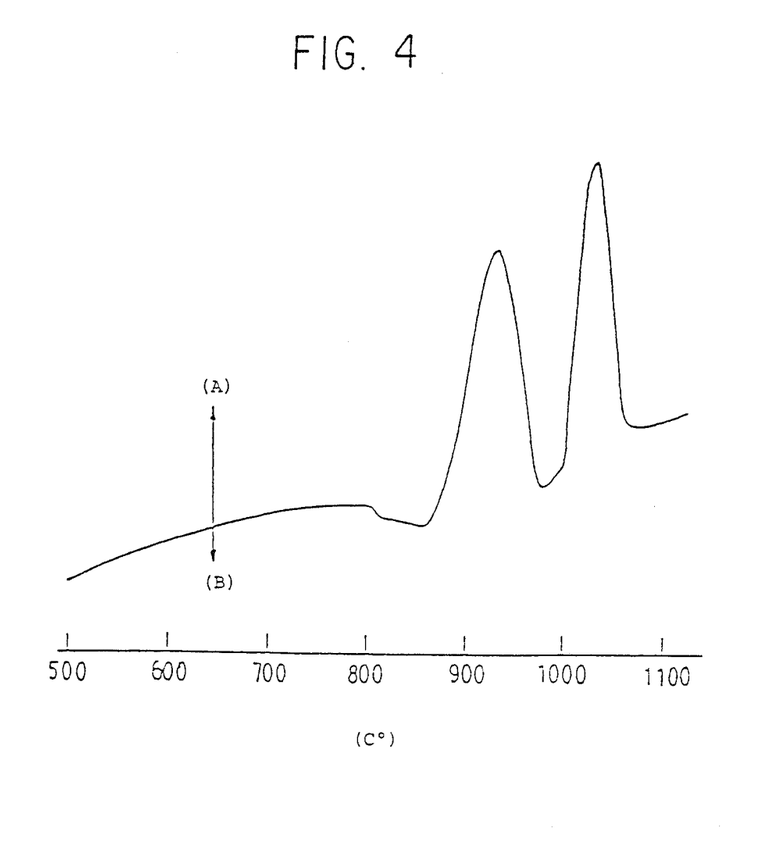
FIG. 4 is a graph showing DTA chart of the same sample as used in the X-ray diffraction test shown in FIG. 3(a). In the graph the abscissa stands for temperature (°C) and a region (A) above the curve is exothermic and a region (B) below the curve is endothermic.

The fact that the powdery product obtained according to the process of this invention by spray thermal decomposition is a cordierite glass powder is obvious from a result of tests revealing that the product is an amorphous substance having a glass transition temperature (Tg). In the tests, a sample identified correctly as cordierite glass was first prepared according to a conventional method of blending silica, alumina and magnesia in a proportion corresponding to the composition of cordierite, melting the powdery blend at 1600° C., pouring the molten mass into water for quenching to effect vitrification and then pulverizing the solid mass to form a cordierite glass powder. In FIGS. 1(a)–1(d) are shown X-ray diffraction patterns of this sample in normal state and in case of being heated at various temperatures. In FIG. 1(a), only a halo pattern in broadened profile is observed which has a peak at a diffraction angle (2θ) of about 24° but a small angle scattering is not observed at an angle smaller than 2θ=5°, thus showing an X-ray diffraction pattern of a typical glass-like powdery substance. In case this glass-like powdery substance was heated, a similar halo pattern of a glass-like substance was shown until 900° C. FIG. 1(b) shows an X-ray diffraction pattern of the sample in that state. FIG. 1(c) shows an X-ray diffraction pattern of the sample heated at 950° C. which corresponds to μ-cordierite crystals. FIG. 1(d) shows an X-ray diffraction pattern of the sample heated at 1050° C. which corresponds to cordierite crystals of hexagonal system. FIG. 2 shows a DTA chart of this sample which has a small endothermic peak at around 800° C., a somewhat broad greater exothermic peak at 940° C. and a sharp great exothermic peak at around 1030° C. In view of FIGS. 1(a)–(d) and FIG. 2, it is noted that the cordierite glass has a glass transition temperature (Tg) at around 800° C., changes from the state of glass to μ-cordierite crystals at 900°–950° C. and further changes to have the crystals of hexagonal system. In FIGS. 3 are shown representative X-ray diffraction patterns of the glass powder of the present invention obtained by spray thermal decomposition of a starting solution in normal state and in case of being heated at various temperatures as in FIGS. 1(a)–1(d). In FIG. 3(a), only a halo pattern in broadened profile is observed which has a peak at $2\theta$=about 24° but a small angle scattering is not observed at an angle smaller than $2\theta = 5°$, thus showing a similar pattern to the case of FIG. 1(a) where the cordierite obtained by a conventional method. This fact apparently suggests that the powdery product obtained in the process of this invention by spray thermal decomposition is not a mere amorphous substance but a substance already converted to a glass-like powder. FIG. 3(b) shows an X-ray diffraction pattern of the powdery product of the present invention heated at 900° C., which shows a halo pattern of a glass-like substance and is similar to the halo pattern shown in FIG. 3(a). FIG. 3(c) shows an X-ray diffraction pattern of the powdery product heated at 950° C., which corresponds to μ-cordierite crystals. FIG. 3(d) shows an X-ray diffraction pattern of the powdery product heated at 1050° C., which corresponds to cordierite crystals of hexagonal system. FIG. 4 shows a DTA chart of the powdery product used in the X-ray diffraction tests shown in FIGS. 3(a)–3(d), which has a small endothermic peak at around 800° C. and two great exothermic peaks at around 930° C. and at around 1030° C. Comparison of FIGS. 3(a)–3(d) with FIGS. 1(a)–1(d) apparently reveals that as a result of X-ray diffraction tests the sample used in the tests shown in FIGS. 1(a)–1(d) is identical with the powdery product used in the tests shown in FIGS. 3(a)–3(d). Furthermore, comparison of FIG. 4 with FIG. 2 reveals that the powdery product has a glass transition temperature (Tg) at around 800° C.

As a result of the above analytical tests, it has been made clear that the powdery product of the present invention obtained by spray thermal decomposition of the starting solution is a glass-like powdery substance although its appearance may vary according to the composition of the starting solution, the content of water and the conditions for spray thermal decomposition.

Figure 6:
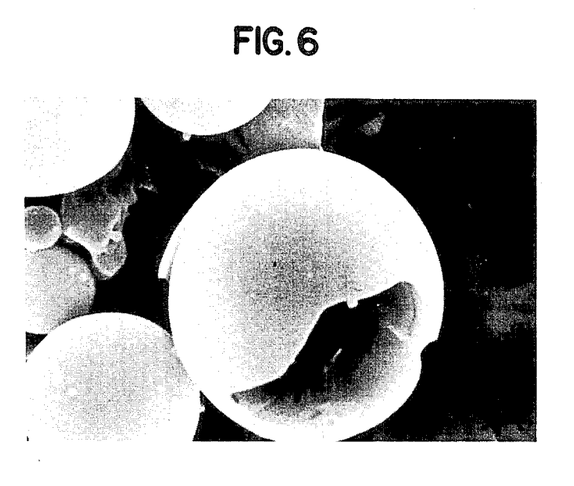
FIG. 6 is a scanning electron micrograph showing a partially broken state of the balloon-like sphere of the cordierite glass powder obtained according to the process of this invention, thereby proving the fact that the balloon shell has a hollow structure.

The structure of the cordierite glass powder of the present invention produced by spray thermal decomposition of the starting solution can easily be understood from scanning electron micrographs shown in FIGS. 5–7.

FIG. 5 is a scanning electron micrograph showing the structure of the cordierite glass powder of the present invention prepared according to the process as described in Example 1. This micrograph apparently shows balloon-like spheres having a diameter of 5 microns or less. The spherical shells are devoid of any pores and has a smooth surface. The size of the balloon-like spheres can be controlled by properly adjusting the diameter of a two fluid nozzle and the flow rates of the starting solution and compressed air. FIG. 6 is a scanning electron micrograph proving that the cordierite glass powder of the present invention has a balloon like structure. This micrograph shows a partially broken state of the balloon of about 15 microns in diameter. The inside of the balloon is usually vacant but a smaller balloon may be present therein in some cases. FIG. 7 is a scanning electron micrograph showing the cordierite glass powder of the present invention obtained from a starting solution containing a larger proportion of water as illustrated in Example 3. The balloon of about 15μ in diameter has a number of open pores in its shell, showing a honeycomb-like structure. The cordierite balloon spheres of this structure was prepared for the first time by the present invention.

The hollow microspherical cordierite glass powder thus produced can be used, irrespective of whether it has a poreless shell or honeycomb-like shell, for the preparation of porous cordierite ceramics. In general, the porous cordierite ceramics are produced by processing the cordierite glass powder to a shaped body, for example, by molding and then firing the shaped body.

Prior to making a shaped body, the hollow spherical cordierite glass powder is preferably subjected to a heat treatment conducted at a temperature below 950° C. for a appropriate period of time, usually within 1–5 hours. The reason why the temperature is limited up to 950° C. is that the heat treatment must be carried out at a temperature lower than the transition temperature of cordierite to crystallization. By maintaining the glass powder at a temperature below 950° C., the glass powder is stabilized against thermal expansion and contraction so that the contraction rate of a shaped cordierite ceramic body to be produced can be minimized.

The cordierite glass powder can be processed to a shaped body or bodies by various means. A typical method for making shaped bodies of the glass powder comprises subjecting the glass powder to molding under pressure. If necessary, the glass powder may be mixed with a binder prior to the molding. In this case, the binder is normally selected from a combustible organic materials such as starch polyvinyl alcohol and the like conventional organic binders. On firing or baking the shaped bodies, these binders are burnt and thus are not retained in the product obtained. As a variant of the molding means, calendering or extrusion can be adopted. These shaping methods are well known and can be carried out in a manner known per se. A preferable shaping means other than molding involves a curing-in-liquid method wherein a slurry of the glass powder in a liquid is agglomerated to spherical particles by treating the slurry with another liquid, a liquid drying method wherein an aqueous slurry of the glass powder is agglomerated to spherical particles by treating the slurry with a dehydrating solvent, a spray drying method wherein a slurry of the glass powder in water or an organic solvent is subjected to spray drying, and a freeze drying method wherein an aqueous slurry of the glass powder is solidified by freezing. These shaping methods are particularly suitable for manufacturing granular shaped bodies and so can be utilized in such case wherein the porous cordierite ceramics are used in a spherical form, for example, as a carrier for gas chromatography or for immobilization of enzymes or microbes.

In some cases, the cordierite glass powder may be shaped in a suitable form, for example, in a vessel in which the resultant ceramics are directly to be used for the desired purpose.

The shaped bodies of the glass powder thus manufactured are then fired (sintered) at a temperature above 1000° C., preferably at 1300°–1460° C. As the melting point of cordierite is about 1470° C., the firing temperature should be controlled to at least 10° C. lower than the melting point, i.e. lower than about 1460° C., or otherwise the balloon-like structure of the cordierite glass powder will be destroyed by fusion of cordierite. The firing time is generally between 1 hour and 10 hours. In the course of the firing treatment, the shaped bodies of the glass powder are changed to polycrystalline fired bodies of cordierite, whereby interstices between the individual balloons remain in the fired bodies as they were and a number of open pores are formed in the shell portion of the individual balloons by foaming of water of crystallization contained in the glass powder and by release of water confined within the balloon and gases formed by thermal decomposition. In the fired bodies, therefore, a great number of open pores are formed in the shell of individual balloons to form an interconnecting open cellular structure as a whole. This phenomenon occurs irrespective of whether the glass powder is in the form of a balloon with a poreless shell having a smooth surface (as shown in FIG. 5) or in the form of a balloon with a shell having a number of open pores formed in a honeycomb structure (as shown in FIG. 7). However, the latter case will more contribute to the porosity of the resultant ceramic bodies as the open pores formed in the shell remain as they were. Such a high porosity as obtained in the present invention can never be expected in a simple manner in the prior art cordierite articles.

In the present invention, the porous cordierite ceramics can be obtained in various forms, for example, particles, granules, block pieces and plates. The shape of the fired articles can further be changed in various mechanical manner, for example, by cutting or boring to manufacture the desired shape for the intended purpose.

From the past, a carrier of naturally occurring diatomaceous earth containing a small amount of $Al_2O_3$ and $Fe_2O_3$ in addition to $SiO_2$ as the predominant component is generally employed as an inorganic solid phase carrier for gas chromatography. However, there are known only a few examples wherein inorganic compounds other than diatomaceous earth are used as solid phase carriers for gas chromatography. Thus, it is particularly noteworthy that a good chromatogram comparable to the case of using a conventional carrier of diatomaceous earth series can be obtained by using the porous cordierite ceramic carrier of the present invention, notwithstanding the carrier of the present invention contains alumina in an amount as much as 25-43% which is usually regarded improper as a carrier for gas chromatography. Since the carrier of the present invention is not of natural origin and can be manufactured synthetically, the composition of the ingredients, purity porosity and other quality are definite and stabilized, so that the product with a stable quality can be supplied. The surface treatment of the carrier, for example, by silanization can be carried out, if necessary, in the same manner as in the case of a conventional carrier using diatomaceous earth.

The porous cordierite ceramics of the present invention are distinguished by their high resistance to heat. Thus, the carrier of the present invention can easily be regenerated by a simple heat treatment. For example, a deactivated carrier on which an enzyme has been immobilized can be regenerated by heating the carrier in a furnace kept at a temperature of about 1000° C., whereby all the organic matters are burnt. The regenerated carrier can be used again without any trouble. Further, this regeneration treatment of the carrier can be repeated without affecting the open cellular structure of the carrier.

Thus, the porous cordierite ceramics of the present invention can advantageously be used repeatedly as carriers for various catalytic reactions and biochemical reactions.

The present invention will now be illustrated in more detail by way of examples and test examples.

EXAMPLE 1

The Formation of Balloon-like Spheres

Various starting solutions are prepared which contained in an organic solvent an alkyl silicate, a magnesium salt and an aluminum salt in a specified composition capable of affording a theoretical composition or cordierite, as shown in Sample Nos. 1, 4, 10, 13, 15, 18, 20, 21, 22, 23 and 27 of Table 1. Each starting solution and a compressed air flow were then supplied respectively at rates of 10-20 ml/min. and 10 liters/min. to a liquid-supplying side and a gas-supplying side of a two-fluid nozzle and sprayed together into the flame of a gas burner whereby very small droplets of the solution with a diameter below several ten microns were instantaneously heated by the flame of the gas burner and by evaporation followed by combustion of the organic solvent in the solution to cause solidification, thermal decomposition and glass-formation. The temperature at the time of the spray thermal decomposition was within the range of 880°-1410° C. The powdery product thus produced was collected from the gaseous stream in a cyclon and subjected to observation with a scanning electron microscope a result of which revealed that the powdery product in each experiment was in the form of balloon-like spheres with a particle size below 25 microns and with a smooth surface. An X-ray diffraction analysis of the product showed in each case only a halo pattern suggestive of a glassy substance. In a thermal analysis of the product by way of DTA, a very small endothermic peak was observed at around 800° C.

EXAMPLE 2

The Formation of Balloon-like Spheres

A starting solution containing the same ingredients in the same composition as shown in Sample No. 1 of Table 1 and a compressed air follow were supplied respectively at rates of 5 ml/min. and 8 liters/min. to a liquid-supplying side and a gas-supplying side of a two-fluid nozzle and sprayed together into a reaction tube placed in an electric furnace previously heated at 1500° C. to effect thermal decomposition and the resultant powdery product was collected from the gaseous stream in a cyclon. The powdery product thus obtained was identified as glassy balloon-like spheres as a result of the analysis.

EXAMPLE 3

The Formation of Balloon-like Spheres with Open Pores

Various starting solutions containing the ingredients in the compositions as shown in Sample Nos. 2, 6, 12, 14, 17, 19, 25 and 29 of Table 1 were prepared and employed for the experiments of spray thermal decomposition in the same manner as described in Example 1. The temperature at the time of combustion was within the range of 730°-1390° C. The powdery product thus produced was collected in a cyclon and subjected to observation with a scanning electron microscope a result of which revealed that in each experiment balloon-like spheres with open pores having a particle size below 30 microns were formed which had about 10-350 pores of 0.01-6 microns in diameter formed in a honeycomb-like structure as shown in FIG. 7. An X-ray diffraction analysis of the product shows in each case a wide halo pattern resulting from a glassy substance. A glass transition temperature was found in DTA of the product.

EXAMPLE 4

The Formation of Balloon-like Spheres with Open Pores

A starting solution containing the same ingredients in the same composition as shown in Sample No. 6 of Table 1 and a compressed air flow were supplied respectively at rates of 5 ml/min. and 8 liters/min. to a liquid-supplying side and a gas-supplying side of a two-fluid nozzle and sprayed together into a reaction tube placed in a tubular electric furnace preheated at 1450° C. to effect thermal decomposition. The resultant powdery product was collected in a cyclon from the gaseous stream. As a result of analysis of the product, it was found that the balloon-like spheres with open pores having a particle size below 12 microns were formed which had 50–150 micropores of less than 2 microns in diameter formed in a honeycomb-like structure as shown in FIG. 7.

EXAMPLE 5

The Formation of Balloon-like Spheres with Open Pores

To a starting solution containing the same ingredients in the same composition as shown in Sample No. 6 of Table 1 was added sodium nitrate in such an amount that its content might be 0.3% by weight in terms of $Na_2O$ relative to cordierite. The solution was then subjected to spray thermal decomposition in the same manner as described in Example 1. As a result of analysis of the resultant powdery product, it was found that the balloon-like spheres with open pores having a particle size below 10 microns were formed which had micropores of less than 2 microns in diameter formed in a honeycomb-like structure as shown in FIG. 7.

EXAMPLE 6

The Preparation of Porous Cordierite Ceramics

Various starting solutions containing the ingredients in the compositions as shown in Sample Nos. 3, 4, 5, 7, 9, 11, 13, 16, 24 and 28 of Table 1 were prepared. Each starting solution and a compressed air flow were supplied at rate of 10–20 ml/min. and 10 liters/min. to a liquid-supplying side and a gas-supplying side of a two-fluid nozzle and sprayed together into the flame of a gas burner whereby very small droplets of the solution were instantaneously heated by the flame of the burner and by evaporation followed by combustion of the alcohol contained in the droplets to cause solidification, thermal decomposition and glass-formation of the droplets. The temperature at the time of the spray thermal decomposition was within the range of 800°–1380° C.

Figure 8:
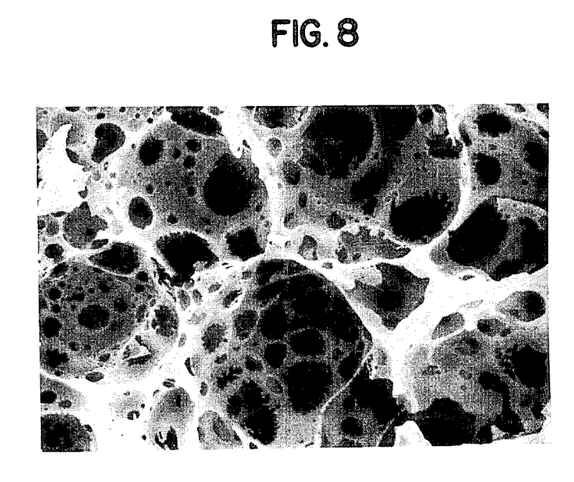
FIG. 8 is a scanning electron micrograph showing the fracture surface of the porous cordierite ceramics of the present invention where individual hollow spheres are interconnected with a number of open pores existing in the spherical shells to form a characteristic interconnecting open cellular structure.

The resultant powdery product in the form of balloon-like spheres with or without open pores was then molded under a forming pressure as shown in Table 2 and the green molded body was sintered at a sintering temperature of 1300°–1450° C. The sintered body obtained in the experiment had interconnecting open cellular structure as shown in FIG. 8. The cells had on their cellular walls open pores of 3 microns in the maximum diameter the majority of which had diameters in the order of submicron. The porosity varied from 48% to 92%.

EXAMPLE 7

The Preparation of Porous Cordierite Ceramics

A starting solution containing the same ingredients in the same composition as shown in Sample No. 5 was prepared. A powdery product obtained by the spray thermal decomposition carried out in the same manner was described in Example 1 was subjected to a heat treatment conducted at 950°0 C. for one hour and then to a molding and sintering treatment conducted under the conditions as referred to in Table 2 whereupon porous cordierite ceramics with open pores of 0.01–25 microns in diameter were obtained which had an interconnecting open cellular structure as described in Example 6.

EXAMPLE 8

The Preparation of Porous Cordierite Ceramics

To a starting solution containing the same ingredients in the same composition as shown in Sample No. 5 of Table 1 was added sodium nitrate in such an amount that its content might to 0.3 by weight in terms of $Na_2O$ relative to cordierite. The solution was then subjected to spray thermal decomposition in the same manner was described in Example 1 and the resultant powdery product was subjected to a molding a sintering treatment conducted under the conditions as referred to in Table 2 whereupon porous cordierite ceramics were obtained as described in Example 7.

TABLE 1

| Sample No. | Composition | | | Organic solvent | Alkyl silicate | Magnesium salt | Aluminum salt | Concentration of solution (mol/l) | Content of water (%) |
|---|---|---|---|---|---|---|---|---|---|
| 1 | | | | Methanol | Tetraethyl silicate | Magnesium nitrate | Aluminum nitrate | 0.5 | 6.0 |
| 2 | | | | " | " | " | " | 0.5 | 50.0 |
| 3 | | | | " | Tetramethyl silicate | " | " | 1.0 | 10.0 |
| 4 | | | | Ethanol | Tetraethyl silicate | " | " | 0.5 | 0.0 |
| 5 | $SiO_2$ | 51.4% | | " | " | " | " | 0.5 | 5.0 |
| 6 | MgO | 13.8% | | " | " | " | " | 0.5 | 8.5 |
| 7 | $Al_2O_3$ | 34.8% | | " | " | " | " | 0.7 | 6.0 |
| 8 | | | | " | " | " | " | 1.5 | 12.0 |
| 9 | | | | " | " | " | " | 2.0 | 50.0 |
| 10 | | | | " | " | Magnesium acetate | " | 0.5 | 4.0 |
| 11 | | | | " | " | " | " | 0.5 | 5.0 |
| 12 | | | | " | " | " | " | 0.5 | 10.0 |
| 13 | | | | Ethanol | Tetraethyl silicate | Magnesium Chloride | ALuminum chloride | 0.5 | 10.0 |

TABLE 1-continued

| Sample No. | Composition | | Organic solvent | Alkyl silicate | Magnesium salt | Aluminum salt | Concentration of solution (mol/1) | Content of water (%) |
|---|---|---|---|---|---|---|---|---|
| 14 | | | " | " | " | " | 0.5 | 20.0 |
| 15 | | | Isopropanol | Tetrapropyl silicate | Magnesium nitrate | Aluminum nitrate | 0.5 | 1.0 |
| 16 | $SiO_2$ | 51.4% | " | " | " | " | 0.5 | 5.0 |
| 17 | MgO | 13.8% | " | " | " | " | 0.5 | 10.0 |
| 18 | $Al_2O_3$ | 34.8% | " | Tetramethyl silicate | " | " | 0.5 | 3.0 |
| 19 | | | " | Tetrabutyl silicate | " | " | 0.5 | 5.0 |
| 20 | | | 2-Methoxy-ethanol | Tetraethyl silicate | " | " | 0.5 | 4.0 |
| 21 | | | Ethylene glycol | " | " | " | 0.5 | 4.0 |
| 22 | | | Acetone | " | " | " | 0.5 | 20.0 |
| 23 | $SiO_2$ MgO | 58.7% 14.2% | Ethanol | Tetraethyl silicate | Magnesium nitrate | Aluminum nitrate | 0.5 | 6.0 |
| 24 | $Al_2O_3$ | 27.1% | " | " | " | " | 0.5 | 10.0 |
| 25 | $SiO_2$ MgO | 58.7% 14.2% | Ethanol | Tetraethyl silicate | Magnesium nitrate | Aluminum nitrate | 1.0 | 20.0 |
| 26 | $Al_2O_3$ | 27.1% | " | " | " | " | 1.5 | 12.0 |
| 27 | $SiO_2$ | 44.6% | " | " | " | " | 0.5 | 6.0 |
| 28 | MgO | 13.3% | " | " | " | " | 0.5 | 10.0 |
| 29 | $Al_2O_3$ | 42.1% | " | " | " | " | 1.0 | 20.0 |

TABLE 2

| Sample No. of Table 1 | Forming pressure (kg/cm$^2$) | Sintering temperature (°C.) |
|---|---|---|
| 3 | 400 | 1400 |
| 4 | 300 | 1350 |
| 5 | 500 | 1400 |
| 7 | 100 | 1400 |
| 9 | 500 | 1300 |
| 11 | 500 | 1400 |
| 13 | 500 | 1450 |
| 16 | 400 | 1400 |
| 24 | 500 | 1400 |
| 28 | 500 | 1400 |

The crystalline phase of the sintered body consisted exclusively of the cordierite phase.

EXAMPLE 9

The Preparation of Porous Cordierite Ceramics

A starting solution containing the same ingredients in the same composition as shown in Sample No. 5 of Table 1 and a compressed air flow were supplied respectively at rates of 5 ml/min. and 8 liters/min. to a two-fluid nozzle and sprayed together into a reaction tube placed in an electric furnace preheated at 1500° C. to effect thermal decomposition whereby a vitreous cordierite powdery product was obtained. The powdery product was then subjected to a molding and sintering treatment in the same manner as described in Example 8 whereupon cordierite ceramics were obtained which had micropores with a diameter below 2 microns formed in an interconnecting open cellular structure as described in Example 8.

EXAMPLE 10

The Preparation of Porous Cordierite Ceramics

A starting solution containing the same ingredients in the same composition as shown in Sample No. 8 was prepared and subjected to spray thermal decomposition in the same manner as described in Example 1 to obtain a cordierite glass powder.

The cordierite glass powder thus obtained were dispersed together with polyvinyl alcohol in an amount of 5% by weight of the glass powder into a mixture of ethanol and water (95:5) and the dispersion was sprayed into n-hexane under agitation kept at −60° C. through a nozzle of 0.2 mm in diameter to form particles in the form of agglonerated powders. The particles thus formed were dried according to a freeze drying method, fired at 1400° C. for 2 hours, cooled slowly and then subjected to a sieving treatment to collect a fraction of 177–250 μm in size for use in the following Test Example 1. The product thus obtained had an interconnecting open cellular structure. The cells had on their cellular walls open pores of several microns in diameter in a structure as shown in FIG. 8. This product was particularly suitable as a carrier, for example, for gas chromatography or catalytic chemical reactions.

EXAMPLE 11

The Preparation of Porous Cordierite Ceramics

A starting solution containing the same ingredients in the same composition as shown in Sample No. 26 of Table 1 was prepared and subjected to spray thermal decomposition in the same manner as described in Example 1 to prepare a cordierite glass powder. Then, this powder was incorporated with 5% by weight of polyvinyl alcohol and the mixture was molded under a forming pressure of 550 kg/cm$^2$ and fired for 2 hours at 1400° C. to form a porous body of cordierite ceramics having the same open cellular structure as described in Example 10. The porous body was pulverized and subjected to a sieving treatment to collect a fraction of 177–250 μm in size for use in the following Test Example 2.

EXAMPLE 12

The Preparation of Porous Cordierite Ceramics

A starting solution containing the same ingredients in the same composition as shown in Sample No. 5 of Table 1 was prepared and well mixed with tetraisopropyl orthotitanate in an amount corresponding to 2% by weight of cordierite in terms of $TiO_2$. This starting solution was subjected to spray thermal decomposition in the same manner as described in Example 1 to prepare a hollow microspherical powdery product, which was then subjected to molding, firing, pulverization and sieving treatments in the same manner as described in Example 11. A fraction of 177–250 μm in size was collected for use in the following Test Example 1. The particles thus obtained were a porous body having an interconnecting open cellular structure. The cells had on their cellular walls open pores having several microns in diameter as described in Example 11. As a result of X-ray analysis, the particles were found to contain cordierite as the main crystalline phase with slight other crystalline phases.

TEST EXAMPLE 1

The porous body obtained in Example 10 (referred to hereinafter as Carrier A) and the particles obtained in Example 12 (referred to hereinafter as Carrier B) were directly coated, without any silanization, with PEG-1000 (a commercially available polyethylene glycol compound) in an amount of 20% by weight of the Carriers according to an evaporator method to prepare packings. A column of 2 m in length and 3 mm in inner diameter was charged with each of these two packings and a separation test was carried out under the following conditions, using methanol, ethanol and n-propanol as samples to be separated:

Carrier gas: helium (He); flow rate 25.2 ml/min.
Amount of the samples introduced: 0.2 μl each
Column pressure: 0.6 Kg/cm$^2$
Column temperature: 70° C.
Detector: a thermal conductivity detector (TCD).

A result of the separation test carried out in Test Example 1 is shown in Table 3. As is evident from Table 3, it is understood that in a separation test using a cordierite ceramics carrier containing a titanium component, the retention time can be shortened to about one third as compared with the case using a carrier having a theoretical composition of cordierite. In each chromatogram, a peak of a desirable normal distribution form, i.e. a peak having symmetrical profiles on both left-hand and right-hand sides was obtained.

TABLE 3

| Samples to be separated | Carrier A Retention time min sec | Carrier B Retention time min sec |
| --- | --- | --- |
| 1 Methanol | 6:32 | 4:08 |
| 2 Ethanol | 8:13 | 5:11 |
| 3 n-Propanol | 15:39 | 9:44 |

TEST EXAMPLE 2

The particles obtained in Example 11 (referred to hereinafter as Carrier C) were coated, without any silanization, with 2% by weight of OV-61 (33% phenyl methyl silicone) in the same manner as described in Test Example 1 to prepare packings. A column of 2 m in length and 3 mm in inner diameter was charged with the packings and a separation test was carried out under the following conditions, using fluoranthene, pyrene and triphenylene as samples to be separated:

Carrier gas: nitrogen (N$_2$); flow rate: 26.9 ml/min.
Amount of the samples introduced: 1 μl (benzene dissolving 1 μg of each sample)
Column pressure: 1.2 Kg/cm$^2$
Column temperature: 300° C.
Detector: a flame ionization detector (FID).

A result of the separation test carried out in Test Example 2 is shown in Table 4. It apparently shows that good results are obtained even at a temperature as high as 300° C. The test in Test Example 2 had been carried out for consecutive 7 days but neither change nor abnormality was found in the shape of peak, base line and the like, and an extremely stable chromatogram was obtained for a long period of time at a high temperature.

TABLE 4

| | Carrier C | |
| --- | --- | --- |
| Samples to be separated | Retention time min sec | Width of peak sec |
| 1 Fluoranthene | 0:48 | 5 |
| 2 Pyrene | 0:53 | 6 |
| 3 Triphenylene | 1:26 | 8 |

TEST EXAMPLE 3

A test for immobilization of aminoacylase was carried out according to the glutaraldehyde method (Academic Press, K. Mosbach, Methods in Enzymology, XLIV, pp. 139–140), using 3 g of porous spheres of cordierite ceramics prepared in Example 10. More precisely, the carrier was treated with a solution of Θ-aminopropyltriethoxysilane for alkylamination. The carrier thus treated was then dipped into a buffer solution containing glutaraldehyde. To this solution was added aminoacylase to effect reaction whereby the aminoacylase was immobilized on the porous cordierite ceramics carrier. The activity of the immobilized aminoacylase was determined by bringing L-methionine formed by the reaction between N-acetyl-DL-methionine and the aminoacylase to a color reaction with ninhydrin and measuring absorbance at 570 nm. As a result of the measurement, the cordierite carrier of the present invention was functionally equivalent to other carriers such as porous glass beads, porous Al$_2$O$_3$ and TiO$_2$ ceramics. Because of the characteristic cellular structure, the cordierite ceramics of the present invention is expected to show excellent properties in immobilization of microbes by physical adsorption.

It is understood that the preceding representative examples may be varied within the scope of the present specification both as to reactants, reaction conditions and ingredients to be added, by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. Porous cordierite ceramics having an interconnecting open cellular structure, which have been formed by the process which comprises providing a starting solution containing in an organic or aqueous organic solvent an alkyl silicate and aluminum and magnesium salts soluble in said organic solvent in a proportion of 44–65% by weight, 25–43% by weight and 10–16% by weight in terms of SiO$_2$, Al$_2$O$_3$ and MgO, respectively, subjecting said starting solution to spray thermal decomposition in the presence of an oxidizing gas to form a hollow microspherical cordierite glass powder, processing said glass powder to a shaped body after an optional heat treatment, and thereafter firing said shaped body at a temperature above 1000° C., wherein said interconnecting open cellular structure comprises individual hollow spheres having spherical shells which are interconnected with a number of open pores existing in the spherical shells.

2. Porous cordierite ceramics according to claim 1, wherein said organic solvent is selected from a lower alkanol with 1-5 carbon atoms, a dihydric or trihydric lower alcohol, a (lower alkoxy) lower alkanol and a lower dialkyl ketone.

3. Porous cordierite ceramics according to claim 1, wherein said alkyl silicate is selected from tetraalkyl silicates in which the alkyl moiety is a lower alkyl with 1-5 carbon atoms.

4. Porous cordierite ceramics according to claim 1, wherein said organic or aqueous organic solvent contains one or more metal compounds capable of affording $Na_2O$, $K_2O$, $TiO_2$ or $ZrO_2$ and soluble in the organic or aqueous organic solvent in an amount up to 5% by weight.

5. Porous cordierite ceramics according to claim 1, wherein said firing of the shaped body is effected at a temperature above the crystallization temperature but below the melting point of cordierite.

6. Porous cordierite ceramics according to claim 1, wherein said spray thermal decomposition is carried out by spraying the starting solution together with an oxidizing gas from a nozzle into a heated reaction zone or the flame of a burner.

7. Porous cordierite ceramics according to claim 1, wherein said processing of the glass powder to a shaped body is effected by molding, extruding, calendering, a curing-in-liquid method, a liquid drying method, a spray drying method or a freeze drying method.

8. Porous cordierite ceramics according to claim 1, wherein said heat treatment is carried out at a temperature below 950° C.

* * * * *